US009868773B2

(12) United States Patent
Titov et al.

(10) Patent No.: US 9,868,773 B2
(45) Date of Patent: Jan. 16, 2018

(54) PEPTIDE FOR TREATMENT OF TYPE 2 DIABETES MELLITUS AND ITS COMPLICATIONS

(71) Applicant: DAPHOT ENTERPRISES LIMITED, Nicosia (CY)

(72) Inventors: Mikhail Ivanovich Titov, Sankt-Peterburg (RU); Ivan Ivanovich Eliseev, Sankt-Peterburg (RU); Valery Gennadyevich Makarov, Sankt-Peterburg (RU); Marina Nikolaevna Makarova, Sankt-Peterburg (RU); Elena Vasilyevna Shekunova, Sankt-Peterburg (RU); Vladimir Aleksandrovich Kashkin, Sankt-Peterburg (RU)

(73) Assignee: DAPHOT ENTERPRISES LIMITED, Nicosia (CY)

( * ) Notice: Subject to any disclaimer, the term of this patent is extended or adjusted under 35 U.S.C. 154(b) by 0 days.

(21) Appl. No.: 15/504,635

(22) PCT Filed: Aug. 4, 2015

(86) PCT No.: PCT/IB2015/001614
§ 371 (c)(1),
(2) Date: Feb. 16, 2017

(87) PCT Pub. No.: WO2016/027157
PCT Pub. Date: Feb. 25, 2016

(65) Prior Publication Data
US 2017/0240610 A1    Aug. 24, 2017

(30) Foreign Application Priority Data

Aug. 21, 2014    (RU) ................ 2014134341

(51) Int. Cl.
| | | |
|---|---|---|
| *A61K 38/00* | (2006.01) | |
| *A61K 38/22* | (2006.01) | |
| *A61K 38/16* | (2006.01) | |
| *C07K 14/00* | (2006.01) | |
| *C07K 14/605* | (2006.01) | |

(52) U.S. Cl.
CPC ............ *C07K 14/605* (2013.01); *A61K 38/00* (2013.01)

(58) Field of Classification Search
CPC ........ A61K 38/00; A61K 38/22; A61K 38/16; C07K 14/605; C07K 14/00
USPC .......................... 514/6.9, 21.3; 530/300, 324
See application file for complete search history.

(56) References Cited

U.S. PATENT DOCUMENTS

| | | | |
|---|---|---|---|
| 5,424,286 A | 6/1995 | Eng | |
| 6,703,359 B1 | 3/2004 | Young et al. | |
| 6,858,576 B1 | 2/2005 | Young et al. | |
| 7,442,682 B2 * | 10/2008 | Kitaura ............... | A61K 9/0014 514/1.1 |
| 2002/0137666 A1 | 9/2002 | Beeley et al. | |
| 2003/0036504 A1 | 2/2003 | Kolterman et al. | |
| 2003/0087821 A1 | 5/2003 | Beeley et al. | |
| 2004/0023871 A1 | 2/2004 | Hiles et al. | |
| 2004/0092443 A1 | 5/2004 | Fridkin et al. | |
| 2004/0209803 A1 | 10/2004 | Baron et al. | |
| 2004/0266678 A1 | 12/2004 | Beeley et al. | |
| 2005/0037958 A1 | 2/2005 | Young et al. | |
| 2005/0043238 A1 | 2/2005 | Young et al. | |
| 2006/0194719 A1 | 8/2006 | Ebbehoj et al. | |
| 2007/0041951 A1 | 2/2007 | Egan | |
| 2009/0239796 A1 * | 9/2009 | Fineman ............. | A61K 9/0019 514/1.1 |
| 2009/0291100 A1 | 11/2009 | Tominaga et al. | |

FOREIGN PATENT DOCUMENTS

| | | |
|---|---|---|
| AU | 2003262628 A8 | 3/2004 |
| AU | 2003297356 A1 | 7/2004 |
| EP | 1419783 A2 | 5/2004 |
| JP | 2002509078 A | 3/2002 |
| JP | 2003519667 A | 6/2003 |
| JP | 2006520747 A | 9/2006 |
| LU | 91342 I2 | 2/2007 |
| MX | 2008015640 A | 1/2009 |
| PT | 1019077 E | 2/2008 |
| RU | 2247575 C2 | 3/2005 |
| WO | 2004029254 A1 | 4/2004 |
| WO | 2004035623 A2 | 4/2004 |
| WO | 2005113744 A1 | 12/2005 |
| WO | 2006044063 A2 | 4/2006 |
| WO | 2006057450 A1 | 6/2006 |

OTHER PUBLICATIONS

Equbal et al, "Novel expression system for Corynebacterium acetoacidophilum and *Escherichia coli* based on the T7 RNA polymerase-dependent promoter," Appl Microbiol Biotechnol., 2013, 97: 7755-7766.*
International Search Report and Written Opinion of corresponding PCT Application No. PCT/IB2015/001614, dated Jan. 18, 2016.

* cited by examiner

*Primary Examiner* — Julie Ha
(74) *Attorney, Agent, or Firm* — Notaro, Michalos & Zaccaria P.C.

(57) ABSTRACT

The invention relates to biotechnology. The exenatide analogue with the formula H-His-Gly-Glu-Gly-Thr-Phe-Thr-Ser-As-Leu-Ser-Lys-Gln-Glu-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro- Pro-Ser-D-Arg-D-Arg-D-Arg-D-Arg-D-Arg-D-Arg-D-Arg-D-Arg-Gly-OH is presented. The invention allows treating and taking preventive measures against diabetes mellitus as well as treating and taking preventive measures against type 2 diabetes mellitus complications, such as diabetic neuropathy, muscular dystrophy and endotheliopathy.

2 Claims, 3 Drawing Sheets

SEQUENCE LISTING

<160> NUMBER OF SEQ ID NOS: 5

<210> SEQ ID NO 1
<211> LENGTH: 48
<212> TYPE: PRT
<213> ORGANISM: Corynebacterium acetoacidophilum
<220> FEATURE:
<221> NAME/KEY: MOD_RES
<222> LOCATION: (40)..(47)
<223> OTHER INFORMATION: D amino acids

<400> SEQUENCE: 1

His Gly Glu Gly Thr Phe Thr Ser Asp Leu Ser Lys Gln Gly Glu Glu

```
                1               5                  10                  15
Glu Ala Val Arg Leu Phe Ile Glu Trp Leu Lys Asn Gly Gly Pro Ser
            20                  25                  30

Ser Gly Ala Pro Pro Pro Ser Arg Arg Arg Arg Arg Arg Arg Gly
        35                  40                  45

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 9-fluorenylmethyloxycarbonyl
<220> FEATURE:
<221> NAME/KEY: MOD_RES
<222> LOCATION: (3)..(4)
<223> OTHER INFORMATION: tButyl

<400> SEQUENCE: 3

Gly Pro Ser Ser Gly
1               5

<210> SEQ ID NO 4
<211> LENGTH: 15
<212> TYPE: PRT
<213> ORGANISM: artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 9-fluorenylmethyloxycarbonyl
<220> FEATURE:
<221> NAME/KEY: MOD_RES
<222> LOCATION: (1)..(3)
<223> OTHER INFORMATION: O-tert-butyl
<220> FEATURE:
<221> NAME/KEY: MOD_RES
<222> LOCATION: (6)..(6)
<223> OTHER INFORMATION: CF3COOH
<220> FEATURE:
<221> NAME/KEY: MOD_RES
<222> LOCATION: (10)..(10)
<223> OTHER INFORMATION: O-tert-butyl
<220> FEATURE:
<221> NAME/KEY: MOD_RES
<222> LOCATION: (11)..(11)
<223> OTHER INFORMATION: tert-butyloxycarbonyl
<220> FEATURE:
<221> NAME/KEY: MOD_RES
<222> LOCATION: (13)..(13)
<223> OTHER INFORMATION: tert-butyloxycarbonyl
<220> FEATURE:
<221> NAME/KEY: MOD_RES
```

```
<222> LOCATION: (14)..(14)
<223> OTHER INFORMATION: triphenylmethyl

<400> SEQUENCE: 4

Glu Glu Glu Ala Val Arg Leu Phe Ile Glu Trp Leu Lys Asn Gly
1               5                   10                  15

<210> SEQ ID NO 5
<211> LENGTH: 13
<212> TYPE: PRT
<213> ORGANISM: artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: tert-Butyloxycarbonyl
<220> FEATURE:
<221> NAME/KEY: MOD_RES
<222> LOCATION: (1)..(1)
<223> OTHER INFORMATION: triphenylmethyl
<220> FEATURE:
<221> NAME/KEY: MOD_RES
<222> LOCATION: (3)..(3)
<223> OTHER INFORMATION: O-tert-butyl
<220> FEATURE:
<221> NAME/KEY: MOD_RES
<222> LOCATION: (5)..(5)
<223> OTHER INFORMATION: tert-butyl
<220> FEATURE:
<221> NAME/KEY: MOD_RES
<222> LOCATION: (7)..(8)
<223> OTHER INFORMATION: tert-butyl
<220> FEATURE:
<221> NAME/KEY: MOD_RES
<222> LOCATION: (9)..(9)
<223> OTHER INFORMATION: O-tert-butyl
<220> FEATURE:
<221> NAME/KEY: MOD_RES
<222> LOCATION: (11)..(11)
<223> OTHER INFORMATION: tert-butyl
<220> FEATURE:
<221> NAME/KEY: MOD_RES
<222> LOCATION: (12)..(12)
<223> OTHER INFORMATION: tert-butyloxycarbonyl
<220> FEATURE:
<221> NAME/KEY: MOD_RES
<222> LOCATION: (13)..(13)
<223> OTHER INFORMATION: triphenylmethyl

<400> SEQUENCE: 5

His Gly Glu Gly Thr Phe Thr Ser Asp Leu Lys Gln Gly
1               5                   10
```

PEPTIDE FOR TREATMENT OF TYPE 2 DIABETES MELLITUS AND ITS COMPLICATIONS

Figure 1:
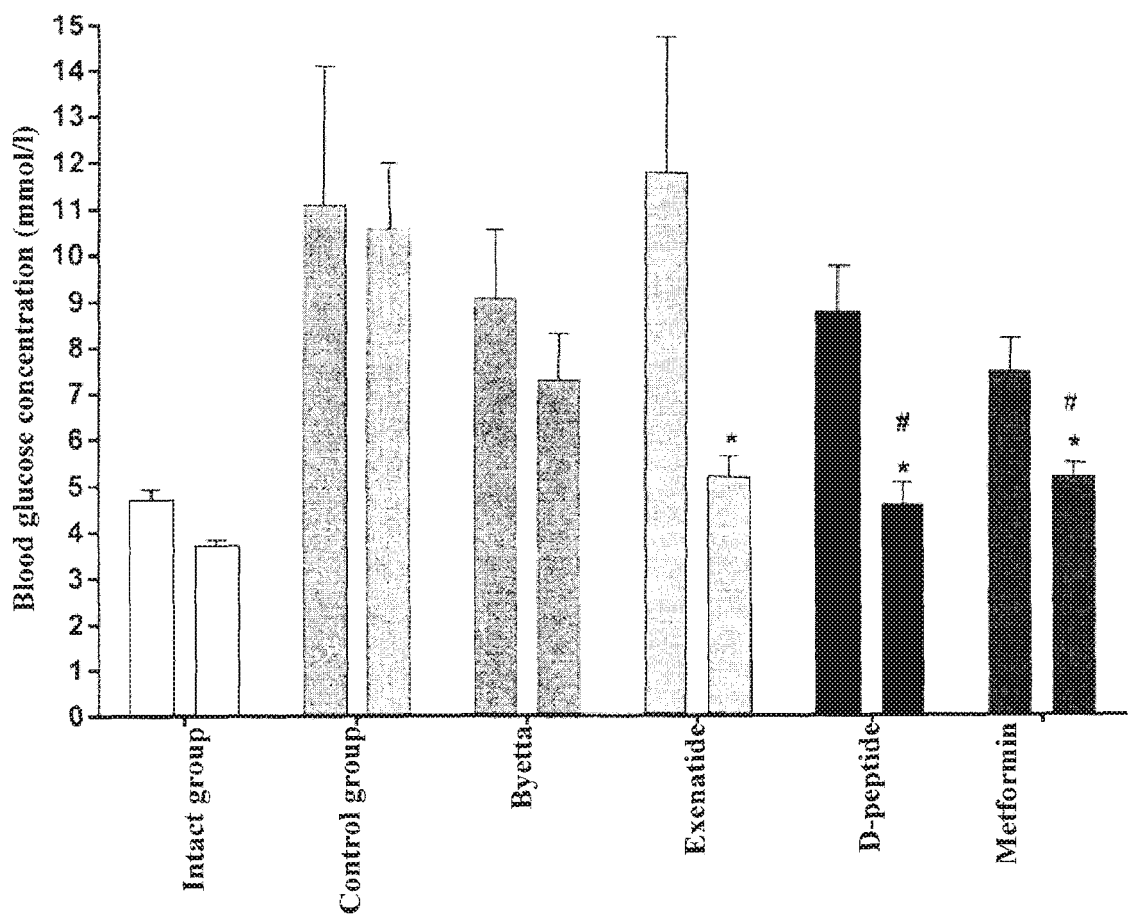

The invention relates to the new exenatide analogue with the following formula

H-His-Gly-Glu-Gly-Thr-Phe-Thr-Ser-Asp-Leu-Ser-Lys-Gln-Gly-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-D-Arg-D-Arg-D-Arg-D-Arg-D-Arg-D-Arg-D-Arg-D-Arg-Gly-OH, which can be used for treatment and prevention of diabetes mellitus, as well as for treatment and prevention of type 2 diabetes mellitus complications such as diabetic neuropathy, muscular dystrophy and endotheliopathy.

The invention relates to medicine and pharmacy and can be used as the drug product for prevention and treatment of 2 type diabetes mellitus, as well as its complications such as diabetic neuropathy, muscular dystrophy and endotheliopathy.

Type 2 diabetes mellitus (DM 2 or non-insulin-dependent diabetes mellitus) is a chronic, multisystemic decease which is mostly manifested in disturbance of carbohydrate metabolism. Hyperglycemia develops as a result of abnormal changes. Besides, there appears a dysfunction of specialized pancreatic gland cells responsible for insulin generation. The main cause for lethality of patients with type 2 diabetes mellitus is firstly development of macrovascular complications (injury of coronary, cerebral and peripheral arteries). Also, DM 2 is one of the main components for development of metabolic syndrome (insulin-resistant or syndrome X) [1]. In recent times number of observations indicating that DM 2 is a pathological marker of Alzheimer dementia development is growing bigger [2].

According to WHO data as of the end of 2013, there are 347 million people suffering from diabetes in the world [3]. 3.4 million people died because of high sugar content in blood in 2004 [4]. Number of fatal cases caused by diabetes complications remained at the same level in 2010 [5]. According to WHO forecasts, diabetes will have become the seventh significant cause of lethality by 2030 [4]. It is believed that type 1 DM can be found among 10-15% of patients in developed countries, and type 2 DM—among 85-90%. But in recent years frequency of type 2 DM in developed countries grows very quickly, whereas number of patients with type 1 DM has not changed significantly. According to the latest WHO data, proportion of type 1 and 2 DM in the world has changed towards increase of frequency of the 2 type DM [5].

The earliest and most frequent complication of diabetes mellitus is diabetic neuropathy [6] which is characterized by nervous system disorder associated with injuries of small blood vessels (vasa vasorum, vasa nervorum). Not only this complication results in work decrement, but also often causes development of serious disabling injuries and death of patients. Pathological process affects all nerve fibers: sensory, motor and vegetal ones. According to data of different authors, diabetic neuropathy can be observed among 90-100% of patients with diabetes mellitus. Frequency of nervous system injuries because of diabetes mellitus is directly proportional to duration of disease, and in some cases it precedes appearance of major clinical signs of diabetes. Thus, 5% of patients with diabetes mellitus onset already have symptoms of nervous system injury that grow in the course of disease reaching up to 60% by 25 years of diabetes duration.

All parts of nervous system are affected due to diabetes mellitus: central nervous system (encephalopathy, myelopathy), peripheral nervous system (poly- and mononeuropathy), and peripheral vegetal nervous system (autonomic neuropathy).

Taking the abovementioned into consideration, it is obvious that development and implementation of medicinal product for therapy of 2 type diabetes itself and its complications in daily practice is promising.

Medicinal treatment of 2 type diabetes mellitus and its complications is currently based on antihyperglycemic drugs which are combined into several groups:

The first group includes two types of medicinal products—thiazolidinediones (rosiglitazone and pioglitazone), PPARγ—agonists, stimulators of nuclear gamma receptors and biguanides (Metformin, Siofor, Avandamet, Bagomet, Glucophage, Metfogamma). Medicinal products of this group enhance sensitivity of cells to insulin, reduce insulin resistance and glucose absorbability by intestinal tract cells, and that is why they are often prescribed for overweight people.

The second group of antihyperglycemic drugs also comprises two types of medicinal products—secondary sulfonylureas (Maninil, Diabeton, Amaril, Glurenorm, Glibinese-retard) that stimulate generation of own insulin, thus increasing its efficiency, and meglitinides (Repaglinide (Novonorm) and Nateglinide (Starlix)) that enhance insulin synthesis by pancreatic gland and also reduce postprandial peaks (increase of sugar level after meal).

The third group of antihyperglycemic drugs includes Acarbose (Glucobay) that reduces glucose absorbability by intestinal tract cells by blocking alfaglucosidase enzyme that splits polysaccharides that are received with meal.

New development in treatment and prevention of DM 2 complications includes direct incretin mimetics, agonists of glucagon-like peptide-1 (GLP-1) receptors and indirect blocking agents of dipeptidyl peptidase of type 4. Direct incretin mimetics include such medicinal products as exenatide (Byetta), liraglutide (Viktoza), albiglutide and dulaglutide. Indirect ones include Sitagliptin (Januvia), Saxagliptin (Onglyza), Linagliptin (Trajenta) and Vildagliptin (Galvus).

Incretin-like medicinal products group poses special interest.

Incretins such as GLP-1 improve beta cells functioning, inhibit inadequately increased secretion of glucagon and provoke increase in glucose-dependent secretion of insulin. Exenatide (exendin-4), being a mimetic of incretin receptors (GLP-1R), is one of medicinal products which efficiency and preventive treatment of non-insulin-dependent diabetes mellitus and its complications has been proved by clinical trials on people.

Exenatide is a polypeptide initially known as exendin-4, the extraction method of which from venom of *Heloderma suspectum* lizard and amino acid sequence of which HGEGTFTSDLSKQMEEEAVRLFIEWLKNGGSSGAP-PPS-NH$_2$ (SEQ ID NO:2) were published in April 1992 for the first time [7]. As a representative of incretin peptides, exendin-4 has a wide potency range, such as glucose-dependent increase in insulin secretion, glucose processing improvement, down-regulation of orexia, slowing down of meal movement from stomach etc.

Use of exenatide for patients with type 2 diabetes mellitus with hyperglycemia suppresses excess secretion of glucagon, but exenatide does not affect regular glucagon response to hypoglycemia.

Exenatide therapy in combination with Metformin and/or medicinal products based on sulfonylurea results in decrease of glucose content in blood in the fasted state, postprandial glucose content in blood, as well as glycosylated hemoglobin value ($HbA_{1c}$), improving glycemic control for these patients.

There are known exenatide fields of use: thus, the USA patent [8] discloses use of exenatide for stimulation of insulin generation with efficiency exceeding that of GLP-1 endogenous hormone. Examples provided in the invention description prove that exenatide is efficient for treatment of diabetes mellitus.

Other therapeutic effects of exenatide have been revealed later: weight reduction [9], gastric motor activity reduction and slowdown of gastric emptying [10, 11], as well as inotropic and diuretic effects of exenatide [12, 13, 14]. Use of exenatide for treatment of polycystic ovary [15, 16, 17], treatment and prevention of nephropathy [18, 19], prevention and treatment of cardiac arrhythmia [20], for bone marrow cell differentiation [21], treatment of diabetes mellitus of the pregnant [22, 23], modulation of triglycerides level and treatment of dyslipidemia [24, 25], suppression of glucagon secretion [26, 27], for differentiation of non-insulin producing cells to the insulin producing [28] are described. The application [29] describes use of exenatide, its agonists and antagonists to affect central nervous system. Patents [30, 31] describe use of exenatide and other antagonists of incretin receptors for reduction of food intake. The application [32] describes stabilized exenatide compositions. Patents [33, 34] describe new applications of exenatide (exendin and its agonists).

All aspects mentioned above indicate high efficiency of exenatide for prevention and treatment of DM 2. However, complications that occur in type 2 diabetes mellitus such as diabetic neuropathy, muscular dystrophy and endotheliopathy are not resolved during therapy both with exenatide and all other abovementioned antihyperglycemic drugs.

That is why there is a task to create new analogues of exenatide that are effective in treatment of complications that occur in the course of the type 2 diabetes mellitus, such as diabetic neuropathy, muscular dystrophy and endotheliopathy.

The closest analogue of the claimed invention is U.S. Pat. No. 5,424,286 [8] selected as a prototype, in which use of incretin mimetics for stimulation of insulin generation is similar to the claimed invention.

The main disadvantage of the known invention is absence of therapeutic effects of incretin mimetics (exenatides) that allow for prevention and treatment of such complications of diabetes mellitus as diabetic neuropathy, muscular dystrophy and endotheliopathy.

Thus, technical result of the claimed invention will be prevention and treatment of such diabetes complications as diabetic neuropathy, muscular dystrophy and endotheliopathy.

Technical result in the claimed invention is achieved by use of the composition according to the formula:

H-His-Gly-Glu-Gly-Thr-Phe-Thr-Ser-Asp-Leu-Ser-Lys-Gln-Gly-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-D-Arg-D-Arg-D-Arg-D-Arg-D-Arg-D-Arg-D-Arg-Gly-OH that has therapeutic effect allowing for prevention and treatment of diabetic neuropathy, muscular dystrophy and endotheliopathy.

The invention is embodied on the following figures.

FIG. 1 is glucose concentration in peripheral blood under the influence of test products, M±m, mmol/l. The first column is the point before the beginning of products injection, the second column is the last day of therapy ($80^{th}$ day).

*—statistically significant differences in groups which administered test products and control group, Bonferroni test with $p<0.05$;

—statistically significant differences in groups between the baseline and the last day of therapy ($80^{th}$ day of products injection), t-test with $p<0.05$.

Figure 2:
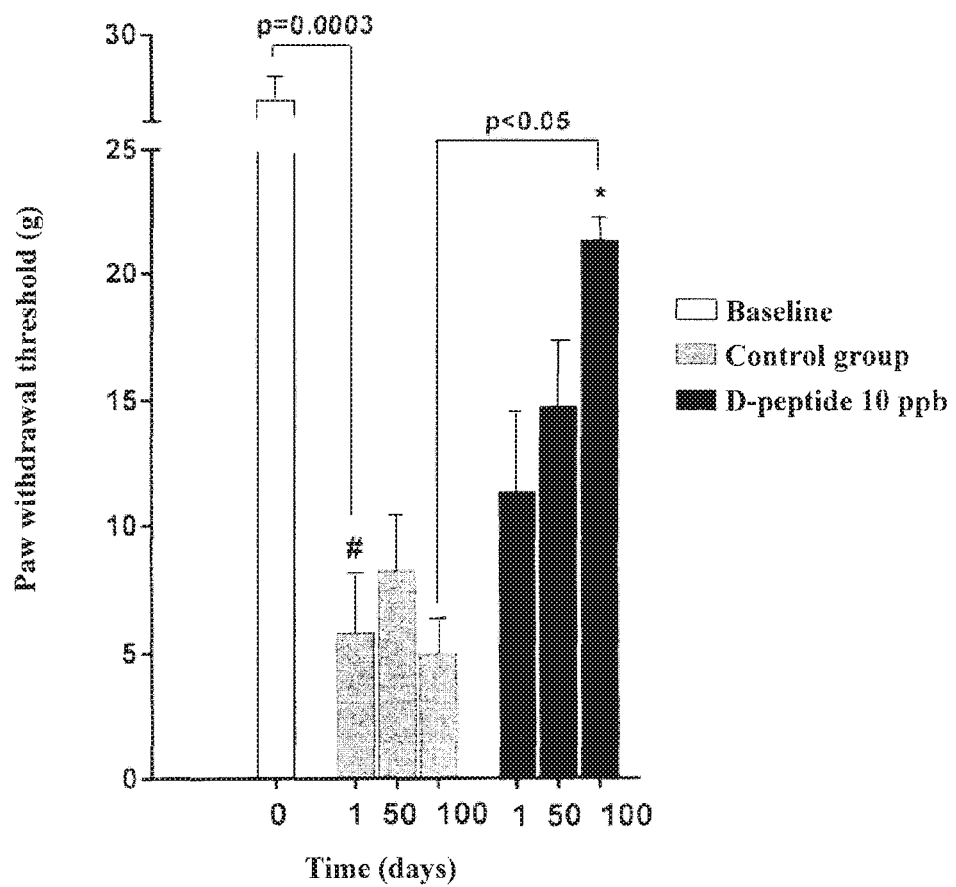

FIG. 2 is impact of D-peptide in the dose of 10 ppb on tactile allodynia on rats with alcohol neuropathy. Animals were injected with D-peptide for 100 days according to the study plan. Tactile allodynia was assessed prior to modeling of alcohol neuropathy on the $1^{st}$ day of product injection, and on the $50^{th}$ and $100^{th}$ day of daily injection. Data are given as a mean threshold value of paw withdrawal (g) (M±m).

Figure 3:
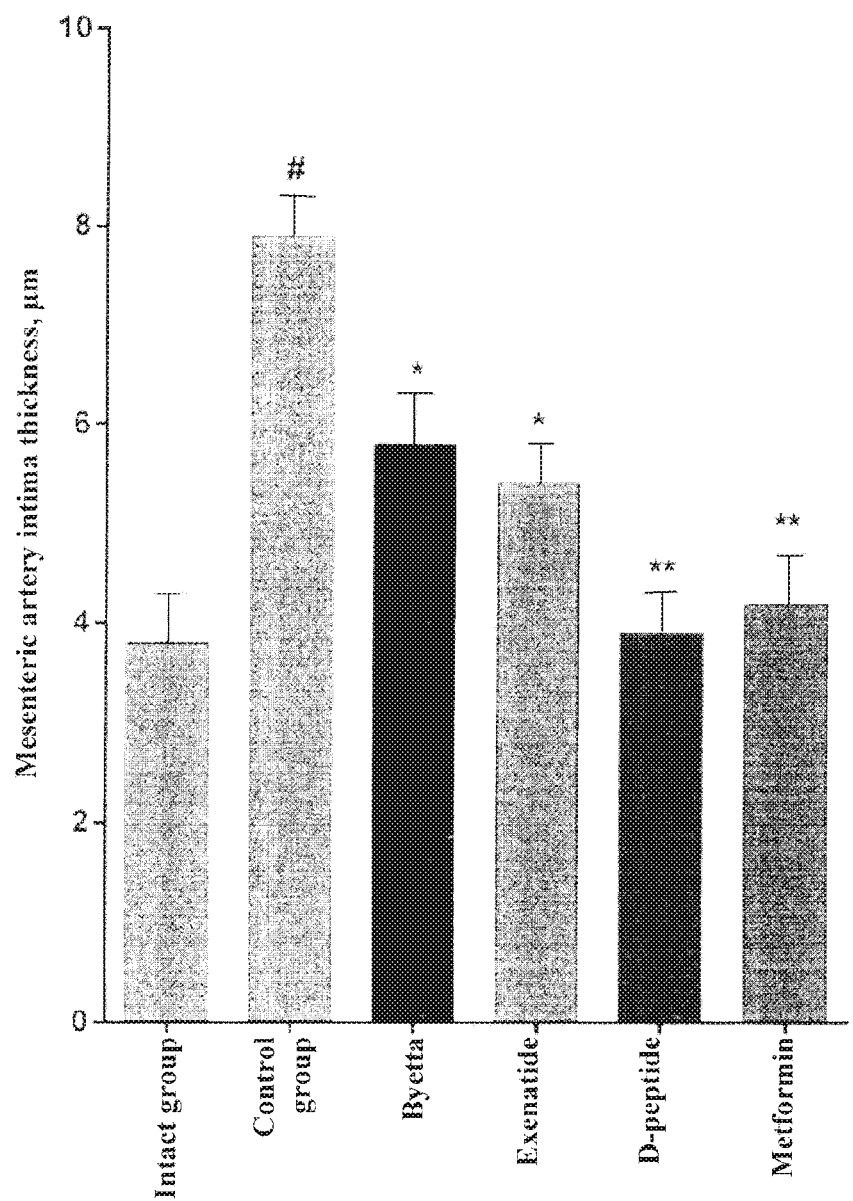

FIG. 3 is mesenteric artery intima thickness after 80-day injection of test products, μm.

—difference from the intact group ($p<0.05$);

*—difference from the control group ($p<0.05$, Bonferroni test);

**—difference from the control group ($p<0.001$, Bonferroni test).

Synthesis of the claimed compound is described in examples 1-5.

EXAMPLE 1

Synthesis of Fmoc-Gly-Pro-Ser(tBu)-Ser(tBu)-Gly-OH 6.0 g of 2-chlorotrityl resin (1.5 mM/g capacity) were suspended in 45 ml of DCM in the solid-phase synthesis reactor, held for 5 mM; the resin was filtered and washed with 2×30 ml of DCM. Solution of 2.95 g (9.9 mM) of Fmoc-Gly-OH and 6 ml (36 mM) of DIPEA dissolved in 30 ml of DCM were added to the resin and stirred for 60 min at the room temperature. The resin was filtered, washed with 2×30 ml of DCM, treated with 2×30 ml of DCM/methanol/DIPEA mixture (17:2:1) for 10 min, and washed with 2×30 ml of DCM and 3×30 ml of DMF. 30 ml of 20% diethylamine solution dissolved in DMF were added to the reactor, held for 20 min, filtered and washed with 5×30 ml of DMF.

Cooled (4° C.) solution of 7.67 g (20.0 mM) of Fmoc-Ser(tBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% diethylamine solution were added to DMF, stirred for 5 min, filtered, washed with 3×30 ml of DMF, 30 ml of 20% diethylamine solution were added to DMF, held for 20 min, filtered and washed with 5×30 ml of DMF.

Cooled (4° C.) solution of 7.67 g (20.0 mM) of Fmoc-Ser(tBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% diethylamine solution were added to DMF, stirred for 5 min, filtered, washed with 3×30 ml of DMF, 30 ml of 20% diethylamine solution were added to DMF, held for 20 min, filtered and washed with 5×30 ml of DMF.

Cooled (4° C.) solution of 6.75 g (20.0 mM) of Fmoc-Pro-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% diethylamine solution were added to DMF, stirred for 5 min, filtered, washed with 3×30 ml of DMF, 30 ml of 20% diethylamine solution were added to DMF, held for 20 min, filtered and washed with 5×30 ml of DMF.

Cooled (4° C.) solution of 3.50 g (20.0 mM) of Fmoc-Gly-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF and 3×30 ml of DCM. After that the resin was treated with 10×30 ml 1% solution of trifluoroacetic acid dissolved in DCM, resulting solutions were combined in a flask containing 30 ml of 10% solution of pyridine in methanol. The mixture was boiled out down to ~50 ml, and 200 ml of water were added to the residue. Obtained sediment was filtered, washed with water and dried. 6.4 g (91%) of 97% pure product according to HELC were obtained.

EXAMPLE 2

Synthesis of Fmoc-Glu(OtBu)-Glu(OtBu)-Glu(OtBu)-Ala-Val-Arg(CF3COOH)-Leu-Phe-Ile-Glu(OtBu)-Trp(Boc)-Leu-Lys(Boc)-Asn(Trt)-Gly-OH 6.0 g of 2-chlorotrityl resin (1.5 mM/g capacity) were suspended in 45 ml of DCM in the solid-phase synthesis reactor, held for 5 min; the resin was filtered and washed with 2×30 ml of DCM. 2.95 g (9.9 mM) solution of Fmoc-Gly-OH and 6 ml (36 mM) of DIPEA dissolved in 30 ml of DCM were added to the resin and stirred for 60 min at the room temperature. The resin was filtered, washed with 2×30 ml of DCM, treated with 2×30 ml of DCM/methanol/DIPEA mixture (17:2:1) for 10 min, and washed with 2×30 ml of DCM and 3×30 ml of DMF. 30 ml of 20% diethylamine solution dissolved in DMF was loaded into the reactor, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 11.93 g (20.0 mM) of Fmoc-Asn(Trt)-OH, 2.98 g (22.0 mM) of DIC dissolved in 30 ml of DMF was loaded into the reactor and stirred for 2 hours at the room temperature. The resin was filtered, washed with 6×30 ml of DMF, 30 ml of 20% diethylamine solution were added to DMF, stirred for 5 min, filtered, washed with 3×30 ml of DMF, 30 ml of 20% diethylamine solution dissolved in DMF were added, held for 20 min, filtered, washed with 5×30 ml of DMF.

Cooled (4° C.) solution of 9.37 g (20.0 mM) of Fmoc-Lys(Boc)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.07 g (20.0 mM) of Fmoc-Leu-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 10.53 g (20.0 mM) of Fmoc-Trp(Boc)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.51 g (20.0 mM) of Fmoc-Glu(OtBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.07 g (20.0 mM) of Fmoc-Ile-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.75 g (20.0 mM) of Fmoc-Phe-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.07 g (20.0 mM) of Fmoc-Leu-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.66 g (20.0 mM) of Fmoc-Arg-OH.HCl, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 6.79 g (20.0 mM) of Fmoc-Val-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 6.23 g (20.0 mM) of Fmoc-Ala-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.51 g (20.0 mM) of Fmoc-Glu(OtBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.51 g (20.0 mM) of Fmoc-Glu(OtBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.51 g (20.0 mM) of Fmoc-Glu(OtBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF and 3×30 ml of DCM. After that the resin was treated with 10×30 ml of 1% solution of trifluoroacetic acid dissolved in DCM, resulting solutions were combined in a flask containing 30 ml of 10% solution of pyridine in methanol. The mixture was boiled out down to ~50 ml, and 200 ml of water were added to the residue. Obtained sediment was filtered, washed with water and dried. 21.8 g (80%) of 95% pure product according to HELC were obtained.

EXAMPLE 3

Synthesis of Boc-His(Trt)-Gly-Glu(OtBu)-Gly-Thr(tBu)-Phe-Thr(tBu)-Ser(tBu)-Asp(OtBu)-Leu-Ser(tBu)-Lys(Boc)-Gln(Trt)-Gly-OH 6.0 g of 2-chlorotrityl resin (1.5 mM/g capacity) were suspended in 45 ml of DCM in solid-phase synthesis reactor, held for 5 min; the resin was filtered and washed with 2×30 ml of DCM. Solution with 2.95 g (9.9 mM) of Fmoc-Gly-OH and 6 ml (36 mM) of DIPEA dissolved in 30 ml of DCM was added to the resin and stirred for 60 min at the room temperature. The resin was filtered, washed with 2×30 ml of DCM, treated with 2×30 ml of DCM/methanol/DIPEA mixture (17:2:1) for 10 min, and washed with 2×30 ml of DCM and 3×30 ml of DMF. 30 ml of 20% diethylamine solution dissolved in DMF were loaded into the reactor, stirred for 5 min, filtered, washed with 3×30 ml of DMF, 30 ml of 20% solution of diethylamine dissolved in DMF were added, held for 20 min, filtered and washed with 5×30 ml of DMF.

Cooled (4° C.) solution of 12.21 g (20.0 mM) of Fmoc-Gln(Trt)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 9.37 g (20.0 mM) of Fmoc-Lys(Boc)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.67 g (20.0 mM) of Fmoc-Ser(tBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.07 g (20.0 mM) of Fmoc-Leu-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.23 g (20.0 mM) of Fmoc-Asp(OtBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.67 g (20.0 mM) of Fmoc-Ser(tBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.95 g (20.0 mM) of Fmoc-Thr(tBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.75 g (20.0 mM) of Fmoc-Phe-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 7.95 g (20.0 mM) of Fmoc-Thr(tBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 5.95 g (20.0 mM) of Fmoc-Gly-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 8.51 g (20.0 mM) of Fmoc-Glu(OtBu)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 5.95 g (20.0 mM) of Fmoc-Gly-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF, 30 ml of 20% solution of diethylamine dissolved in DMF were added, stirred for 5 min, filtered, washed with 3×30 ml of DMF, 30 ml of 20% diethylamine solution dissolved in DMF were added, held for 20 min, filtered and washed with 5×30 ml of DMF.

Cooled (4° C.) solution of 9.95 g (20.0 mM) of Boc-His(Trt)-OH, 2.98 g (22.0 mM) of HOBt and 3.42 ml (22.0 mM) of DIC dissolved in 30 ml of DMF was loaded into the reactor and stirred for 2 hours at the room temperature. The resin was filtered, washed with 6×30 ml of DMF and 3×30 ml of DCM. After that the resin was treated with 10×30 ml of 1% solution of trifluoroacetic acid dissolved in DCM, resulting solutions were combined in a flask containing 30 ml of 10% solution of pyridine in methanol. The mixture was boiled out down to ~50 ml, and 200 ml of water were added to the residue. Obtained sediment was filtered, washed with water and dried. 20.9 g (85%) of 95% pure product according to HELC were obtained.

EXAMPLE 4

Synthesis of 14-glycine-exendin-4 (*Heloderma suspectum*)-(1-39)-peptidyl-octa-D-arginyl-glycine H-His-Gly-Glu-Gly-Thr-Phe-Thr-Ser-Asp-Leu-Ser-Lys-Gln-Gly-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-D-Arg-D-Arg-D-Arg-D-Arg-D-Arg-D-Arg-D-Arg-D-Arg-Gly-OH 2.0 g of 2-chlorotrityl resin (1.5 mM/g capacity) were suspended in 15 ml of DCM in the solid-phase synthesis reactor, held for 5 min; the resin was filtered and washed with 2×10 ml of DCM. Solution with 0.98 g (3.3 mM) of Fmoc-Gly-OH and 2 ml (12 mM) of DIPEA dissolved in 10 ml of DCM was added to the resin and stirred for 60 min at the room temperature. The resin was filtered, washed with 2×30 ml of DCM, treated with 2×10 ml of DCM/methanol/DIPEA mixture (17:2:1) for 10 min, and washed with 2×10 ml of DCM and 3×10 ml of DMF. 10 ml of 20% diethylamine solution dissolved in DMF were added to the reactor, stirred for 5 min, filtered, washed with 3×10 ml of DMF, 10 ml of 20% solution of DMF were added, held for 20 min, filtered and washed with 5×10 ml of DMF.

Cooled (4° C.) solution of 2.60 g (6.0 mM) of Fmoc-D-Arg-OH.HCl, 0.98 g (7.2 mM) of HOBt and 1.12 ml (7.2 mM) of DIC dissolved in 10 ml of DMF was loaded into the reactor and stirred for 2 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 2.60 g (6.0 mM) of Fmoc-D-Arg-OH.HCl, 0.98 g (7.2 mM) of HOBt and 1.12 ml (7.2 mM) of DIC dissolved in 10 ml of DMF was loaded into the reactor and stirred for 4 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 3.46 g (8.0 mM) of Fmoc-D-Arg-OH.HCl, 1.35 g (10.0 mM) of HOBt and 1.56 ml (10.0 mM) of DIC dissolved in 10 ml of DMF was loaded into the reactor and stirred for 3 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 3.46 g (8.0 mM) of Fmoc-D-Arg-OH.HCl, 1.35 g (10.0 mM) of HOBt and 1.56 ml (10.0 mM) of DIC dissolved in 10 ml of DMF was loaded into the reactor and stirred for 4 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 3.46 g (8.0 mM) of Fmoc-D-Arg-OH.HCl, 1.35 g (10.0 mM) of HOBt and 1.56 ml (10.0 mM) of DIC dissolved in 10 ml of DMF was loaded into the reactor and stirred for 10 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 4.33 g (10.0 mM) of Fmoc-D-Arg-OH.HCl, 1.62 g (12.0 mM) of HOBt and 1.88 ml (12.0 mM) of DIC dissolved in 10 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 4.33 g (10.0 mM) of Fmoc-D-Arg-OH.HCl, 1.62 g (12.0 mM) of HOBt and 1.88 ml (12.0 mM) of DIC dissolved in 10 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 mM, filtered and washed with 5×10 ml of DMF.

Cooled (4° C.) solution of 4.33 g (10.0 mM) of Fmoc-D-Arg-OH.HCl, 1.62 g (12.0 mM) of HOBt and 1.88 ml (12.0 mM) of DIC dissolved in 10 ml of DMF was loaded into the reactor and stirred for 16 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 3.07 g (8.0 mM) of Fmoc-Ser(tBu)-OH, 1.35 g (10.0 mM) of HOBt and 1.56 ml (10.0 mM) of DIC dissolved in 30 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 2.70 g (8.0 mM) of Fmoc-Pro-OH, 1.35 g (10.0 mM) of HOBt and 1.56 ml (10.0 mM) of DIC dissolved in 30 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 2.70 g (8.0 mM) of Fmoc-Pro-OH, 1.35 g (10.0 mM) of HOBt and 1.56 ml (10.0 mM) of DIC dissolved in 30 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 2.70 g (8.0 mM) of Fmoc-Pro-OH, 1.35 g (10.0 mM) of HOBt and 1.56 ml (10.0 mM) of DIC dissolved in 30 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 2.49 g (8.0 mM) of Fmoc-Ala-OH, 1.35 g (10.0 mM) of HOBt and 1.56 ml (10.0 mM) of DIC dissolved in 30 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 5.90 g (8.0 mM) of Fmoc-GlyProSer(tBu)Ser(tBu)Gly-OH (product from Example 1), 1.62 g (12.0 mM) of HOBt and 1.88 ml (12.0 mM) of DIC dissolved in 30 ml of DMF was loaded into the reactor and stirred for 12 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 11.35 g (4.0 mM) of Fmoc-Glu(OtBu)-Glu(OtBu)-Glu(OtBu)Glu(OtBu)AlaValArg(HCl)LeuPheIleGlu(OtBu)Trp(Boc)LeuLys(Boc)Asn(Trt)Gly-OH (product from Example 2), 0.81 g (6.0 mM) of HOBt and 0.95 ml (6.0 mM) of DIC dissolved in 30 ml of DMF was loaded into the reactor and stirred for 24 hours at the room temperature. The resin was filtered, washed with 6×10 ml of DMF, 10 ml of 20% solution of diethylamine dissolved in DMF were added, stirred for 5 min, filtered, washed with 3×10 ml of DMF, 10 ml of 20% diethylamine solution dissolved in DMF were added, held for 20 min, filtered and washed with 5×10 ml of DMF.

Cooled (4° C.) solution of 9.94 g (4.0 mM) of Boc-His(Trt)Gly-Glu(OtBu)GlyThr(tBu)PheThr(tBu)Ser(tBu)Asp(OtBu)LeuSer(tBu)Lys(Boc)Gln(Trt)Gly-OH (product from Example 3), 0.81 g (6.0 mM) of HOBt and 0.95 ml (6.0 mM) of DIC dissolved in 30 ml of DMF was loaded into the reactor and stirred for 24 hours at the room temperature. The resin was filtered, washed with 6×20 ml of DMF, 4×20 ml of DCM, dried, added 50 ml of TFA/TIS/EDT/H2O mixture (97:1:1:1), held for 4 hours at the room temperature, filtered, washed with 3×20 ml of trifluoroacetic acid, combined filtrates were boiled out down to ~20 ml, added 60 ml of dry ether to the residue. Obtained sediment was filtered, washed with ether on a filter and dried. The obtained product was dissolved with 50 ml of water, and the mixture was frozen and lyophilized. The lyophilizate was dissolved with 40 ml of water and applied to Amberlite IRA-400 (Cl form) ion exchange resin column. The column was washed with water, fractions that contain the product were boiled out down to ~50 ml and applied to Water X-Bridge C18 reverse-phase column, 10 μm, 127 Å, 50×250 mm. Elution was performed at eluent flow of 50 ml/min. Phase A: 0.1% HCl/H2O, B: acetonitrile. Gradient: 0% (B)-70% (B) during 70 min. Fractions containing the main product were combined, boiled out down to ~50 ml, frozen and lyophilized. 3.9 g (20%) of 97.5% pure product (HELC) were obtained. Mass spectrum: calculated for $C_{231}H_{374}N_{82}O_{70}$ MH+ 5420.98, MH+ 5420.80 was obtained Amino acid analysis: alanine 2.02 (2), arginine 9.0 (9), aspartic acid+asparagine 2.05 (2), glutamic acid+glutamine 5.80 (6), glycine 7.25 (7), histidine 1.02 (1), isoleucine 1.03 (1), leucine 2.96 (3), lysine 2.07 (2), phenylalanine 2.05 (2), proline 4.10 (4), serine 4.85 (5), threonine 1.90 (2), and valine 1.02 (1).

EXAMPLE 5

Synthesis of H-His-Gly-Glu-Gly-Thr-Phe-Thr-Ser-Asp-Leu-Ser-Lys-Gln-Gly-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-D-Arg-D-Arg-D-Arg-D-Arg-D-Arg-D-Arg-D-Arg-D-Arg-Gly-OH using the *Corynebacterium acetoacidophilum* strain.

1.1. Design of pBSΔCg10278 vector for deletion of Cg10278 gene coding PBP1a

Genome sequence of *C. acetoacidophilum* ATCC 13032 and nucleotide sequence of Cg1278 gene coding PBP1a penicillin-binding protein are known (GenBank, inventory number BA000036 (version BA000036.3 GI: 42602314, locus_tag=<<NCg10274>>)). P1, P2, P3 and P4 primers were synthesized with reference to this sequence. With help of PCR, using chromosome DNA as the matrix of *C. acetoacidophilum* ATCC 13869 strain prepared in conventional method (Saito H. and Miura K. I., Biochim. Biophys. Acta, 1963, 72:619-629) and primers P1, P2, P3 and P4 a fragment (about 1 tpn) from 5' side and a fragment (about 1 tpn) from 3' side were obtained from Cg10278 that codes PBP1a respectively. Then, with help of the PCR and using both DNA fragments as matrix and P1 and P4 primers, a DNA fragment (about 2 tpn) consisting of both fragments combined with each other was obtained. Recognition sites for restriction enzimes BamH I and Xba I respectively were applied. Pyrobest DNA polymerase (manufactured by Takara Bio) and conditions recommended by the manufacturer were used for the PCR. This DNA fragment was treated with BamH I and Xba I restriction enzymes, and, for the purpose of acquisition of pBSΔCg10278 vector for deletion of Cg0278 gene, it was added to BamH I-Xba I pBS4 site described in WO 2005/113744. DNA Ligation Kit Ver. 2.1 (manufactured by Takara Bio) and conditions recommended by the manufacturer were used for ligation.

1.2. Design of PBP1a-less Strain

*C. acetoacidophilum* YDK010 strain described in WO 2004/029254 was transformed with the designed pBSΔCg10278 vector. *C. acetoacidophilum* YDK010 strain is a strain lacking a PS2 cell top layer protein of *C. acetoacidophilum* AJ12036 (FERM BP-734) (WO 2004/029254). The strain was chosen from transformants obtained in accordance with the description of WO 2005/113744 and WO 2006/057450 for the purpose of obtaining YDK010ΔPBP1a strain lacking Cg1278 gene.

Examples shown below relate to pharmacological tests of obtained peptide.

The purpose of the study is revelation of antihyperglycemic activity and preventive and therapeutic effects of the claimed compound (hereinafter referred to as "D-peptide") in complications in the basis of the model of chemical experimental diabetes induced by a single injection of Streptozocin (STZ) and nicotinamide to male rats [35].

The following medicinal products were used for comparison:

1. Byetta® (as a reference medicinal product for prevention and treatment of DM 2 complications) is a transparent solution for subcutaneous injection, 250 μg/1 ml: prefilled syringes 1.2 ml of BAXTER Pharmaceutical Solutions.
2. Synthetic exenatide substance
3. Metformin (Siofor® 500) (as a conventional antihyperglycemic product of biguanides).

Applied Reagents and Materials

A kit of reagents for determination of the glycosylated hemoglobin level ("Phosphosorb" LLC, Russia).

Applied Equipment

1. Laboratory medical dosing device, 10-100 μl.
2. Laboratory medical dosing device, 100-1,000 μl.
3. Microcentrifuge Z 216 MK (Hermle Labortechnik GmbH, Germany).
4. Glucose meter OneTouch UltraEasy® (LifeScan, USA).
5. Dipsticks OneTouch Ultra® (LifeScan, USA).
6. Von Frey hairs (Stoelting, USA).

Animals

| Animal species: | Outbred male rats |
| --- | --- |
| Source: | Russian Academy of Medical Sciences Farm of laboratory animals "Rappolovo" |
| Weight of animals prior to beginning of study | 140-200 g |
| Quantity of animals: | 50 |
| Veterinary certificate: | 247 No. 0109645 dated Jul. 31, 2013 |

Adaptation and Selection of Animals

Prior to the beginning of study, laboratory animals were held 7 days for adaptation with group management in cages. During this period the animals were controlled daily for clinical condition by way of visual examination. Animals with abnormalities detected in examination were not included into experimental groups. Before the study was commenced, the animals which met criteria of inclusion into the experiment were grouped.

Grouping

Selection of animals was performed using the method of modified block randomization [36]. For this purpose all animals delivered from the farm were randomly put into randomization block cells (quantity of cells of the randomization block is divisible by quantity of groups in the experiment). Then, using the random number generator (statistical program Statistica 6.0), the list of data containing numbers of cells with animals and their corresponding group numbers was obtained, wherein animals were put subsequently [36].

Identification of Animals

Cage labels included sex, quantity of animals, experiment start date and group name. Each animal selected for the study was assigned with an individual number by applying a mark on the tail.

Animals were held under standard conditions in accordance with rules established by the Ministry of Healthcare of the USSR dated 6 Jul. 1973 as to arrangement, equipping and management of experimental and biological clinics (vivaria) and GOST R 53434-2009.

Animals were held in standard transparent plastic cages in groups of 5 individuals on the bedding; cages were covered with steel screens with a feeding cavity. The floor area for one animal comprised 440 cm$^2$ (minimum allowable area is 250 cm$^2$).

"Feed for animal management" HK-120-1 prepared per GOST R 50258-92 according to regulations approved by the Order of the Ministry of Healthcare of the USSR No. 755 dated 12 Aug. 1977 was added ad libitum to the feeding cavity of the steel cage screen (when measuring glucose level, animals were deprived of feed for 18 hours). The veterinary certificate No. 247 No. 0294922 ("Aller Petfood" LLC, Russia), as well as the certificate of conformity No. POCRU.ПР98.H00093/0051289, validity period from 17.05.2011 till 16.05.2014.

Animals were supplied with water purified according to the SOP ОЖ-ОС-4 and rationed by organoleptic properties, pH values, dry residue, reducing substances, carbon dioxide, nitrates and nitrites, ammonia, chlorides, sulfates, calcium and heavy metals in accordance with the SOP АБ-38 on the basis of GOST 51232-98 "Drinking water. General requirements for organization and quality control methods". Water in standard drinking troughs with steel hand lifting cover was supplied ad libitum.

Wood pellets 6 mm ("ZooSPb" LLC, Russia) were used as the bedding. Animals were held under controlled environmental conditions (temperature of 19.5-21° C. and relative humidity of 61-75%). Light regime comprised 12 hours of light and 12 hours of darkness. Ventilation regime providing approximately 15 volumes of premises per hour, $CO_2$ concentration of not more than 0.15 vol. %, ammonia of not more than 0.001 mg/l was adjusted. Air temperature and humidity were recorded daily. No significant deviations of these parameters were observed during the carry-on period and in the course of experiment.

Study Design

Characteristics of study groups, route and duration of administration of test substances

| Group No. | Sex, q-ty of animals | Administered substance | Dose | Route and duration of administration |
|---|---|---|---|---|
| 1 | M 5 | — | — | Subcutaneously, daily, once a day during 80 days |
| 2 | M 5 | Distilled water | — | |
| 3 | M 10 | Byetta ® | 4.5 ppb | |
| 4 | M 10 | Exenatide | 4.5 ppb | |
| 5 | M 10 | D-peptide | 6.0 ppb | |
| 6 | M 10 | Metformin (Siofor ® 500) | 85.7 ppm | Intragastrically, daily, once a day during 80 days |

In accordance with the experiment schedule, animals underwent induction of experimental diabetes mellitus using single injection of Streptozotocin (STZ) abdominally in the dose of 65 ppm previously diluted in citrate buffer (pH=6.5) on the day 0. All animals were injected abdominally with nicotinomide in the dose of 230 ppm (5% solution) 2 hours before it [35, 37].

Glucose level in peripheral blood was measured on fasting rats (animals were deprived of feed for a night) prior to pathology induction, then 1, 3 and 9 days after pathology induction. After beginning of injection of test substances, glucose level was measured every 10 days and on the day of euthanasia. Body weight recording was carried out on the same days as glucose level measurement. The allodynia test was performed on the $60^{th}$, $70^{th}$ and $80^{th}$ days of injection of medicinal products during experiment. In case of alcohol neuropathy, the tactile responsiveness test was performed on the $1^{st}$, $50^{th}$ and $100^{th}$ day of injection of medicinal products.

A sample of venous blood was taken to determine the glycosylated hemoglobin level of animals on the day of euthanasia. The following organs were also taken for pathomorphological study: sciatic nerve, part of mesentery artery, part of retina artery, part of gastrocnemius muscle and pancreatic gland.

Experiment and Operation Schedule

| Operation | Experiment day | | | | | | | | | | |
|---|---|---|---|---|---|---|---|---|---|---|---|
| | 0 | 1 | 10 | 20 | 30 | 40 | 50 | 60 | 70 | 80 | 90 |
| Pathology induction | yes | | | | | | | | | | |
| Body weight recording | | yes | yes | yes | yes | yes | yes | yes | yes | yes | |
| Measurement of glucose level in peripheral blood* | | yes | yes | yes | yes | yes | yes | yes | yes | yes | |
| Allodynia test | yes | | | | | | | yes | yes | yes | yes |
| Injection of medicinal products | | yes | yes | yes | yes | yes | yes | yes | yes | yes | |
| Measurement of glycosylated hemoglobin | | | | | | | | | | | yes |
| Euthanasia | | | | | | | | | | | yes |

EXAMPLE 6

Determination of Glucose in Blood of Experimental Animals

Glucose level measurement in peripheral blood of rats was conducted using the glucose meter OneTouch® and dipsticks OneTouch® by the glucose oxidase test. Rats were deprived of feed, but not water for a night before glucose level measurement. The measurement process was as follows: an animal with a required mark was removed from the cage, its tail was treated with bactericidal agent, a vein was punctured using a syringe needle, and the glucose meter with a dipstick was brought in place when a blood drop was effused. Obtained data was entered into the initial card.

It can be seen on FIG. 1 that the general tendency for glucose concentration reduction was observed on the background of application of test products. Two-way analysis of variance (ANOVA) with repeated measurements revealed statistically significant impact of test products on glucose concentration in peripheral blood ($F_{4,25}=3.49$, $p=0.02$). Further intergroup comparison showed significant difference of the group injected with Metformin starting from the $20^{th}$ day of product injection ($p<0.05$, Bonferroni test), as well as groups injected with claimed peptide (D-peptide) starting from the $40^{th}$ day of product injection ($p<0.05$, Bonferroni test) as compared to the control group.

Paired comparison between glucose baseline prior to therapy (point "0") and the last day of therapy ($80^{th}$ day) showed statistically significant difference in groups which were injected with Metformin ($p=0.017$, t-test) and D-peptide ($p=0.011$, t-test) (FIG. 1).

Finally, it may be concluded that claimed D-peptide had antihyperglycemic effect during therapy with duration of 80 days starting from the 40$^{th}$ day of injection. Incretin-like product, exenatide, also showed antihyperglycemic effect starting from the 50$^{th}$ day of injection, though its intensity was lower than that of D-peptide. Injection of Byetta® showed no impact on glucose level in peripheral blood, but reference product Metformin showed antihyperglycemic properties starting from the 20$^{th}$ day of therapy as expected.

EXAMPLE 7

Determination of Glycosylated Hemoglobin in Peripheral Blood

Determination of glycosylated hemoglobin in venous blood was conducted using the kit of reagents "Diabetes Test, HbA$_{1c}$" ("Phosphosorb" LLC, Russia) by the method of affinity chromatography of glycosylated and non-glycosylated hemoglobin fractions in rat blood hemolysate.

Blood samples for determination of glycosylated hemoglobin in hemolysate of animal red blood cells were taken from the tail vein of experimental animals on the 81$^{st}$ day of daily injection of test products. Obtained data are given in table 1.

TABLE 1

Content of glycosylated hemoglobin in animal blood, %, M ± m

| Group | n | Glycosylated hemoglobin, % |
|---|---|---|
| Intact group | 5 | 4.2 ± 0.59 |
| Control group | 4 | 15.6 ± 1.63# |
| Byetta ® | 4 | 8.1 ± 1.16* |
| Exenatide | 4 | 7.9 ± 2.03* |
| D-peptide | 4 | 5.5 ± 0.53* |
| Metformin | 6 | 5.7 ± 0.25* |

Note:
differences are statistically significant in comparison with the intact group, t-test for independent variables with p < 0.05,
*differences are statistically significant in comparison with the control group, Bonferroni test with p < 0.05.

It can be seen in the data of table 1 that a statistically significant increase of HbA$_{1c}$ concentration by 4 times was observed in control group animals in comparison with the intact group (p=0.0002, t-test). Measurement data characterize apparent development of experimental pathology.

A statistically significant reduction of HbA$_{1c}$ concentration was established on the background of application of test products ($F_{4.17}$=11.83, p<0.0001). Further intergroup comparison revealed maximum therapy effect in groups which administered claimed D-peptide (p<0.0001) and Metformin (p<0.0001), while this effect was not so apparent in groups which underwent therapy with Byetta® and Exenatide (p=0.0018 and p=0.0015 respectively).

EXAMPLE 8

Assessment of Tactile Allodynia on Rats with Diabetic Neuropathy

A rat was put into a plastic cage with a grating floor made of metal wire and left in this cage for 5 minutes to extinguish orientation response. Determination of mean effective threshold of tactile responsiveness was conducted by the method of Chaplan et al. [38] using the kit consisting of 8 standard von Frey hairs (Stoelting, USA). Hair coarseness expressed as minimum force which is required for hair bending increased logarithmically with absolute values of 0.692 to 28.840 g.

Threshold of each rat was initially determined on the left paw, and then on the right paw. A hair end touched the middle of the plantar surface on the paw with the force required for hair bending, and it was left in this position for 6-8 seconds. Positive response was recorded if the animal withdrew its paw abruptly during touching, or removal of a hair was followed by sharp paw bending.

Testing was started from application of a hair corresponding to the force of 3.630 g. Then stimuli (hairs) were used in the increasing and decreasing sequence. The hair with the least coarseness was used in case of positive response, while the hair with the largest coarseness was used in case of negative response. 4 more hairs were used according to the same principle after initial determination of sensitivity threshold.

Psychophysiological mean effective threshold of tactile responsiveness was calculated by the method described by Dixon [39].

Table 2 presents results of experiments on study of impact of 80-day injection of test products on development degree of tactile allodynia.

In completed experiments by the day 60 of injection of medicinal products, manifestation of tactile allodynia in the control group was maximum ($F_{1;14}$=669.8, p<0.0001) which indicates the established model of diabetic neuropathy with apparent pain syndrome.

Statistical processing by two-way analysis of variance with repeated measurements which allowed determining significance of the factor "injection of medicinal products" on expression of tactile allodynia was carried out for further assessment of obtained results ($F_{4.43}$=10.93; p<0.0001). Further intergroup comparison (Bonferroni test) showed decrease in tactile allodynia intensity in the group which administered D-peptide starting from the 60$^{th}$ day of injection. Table 3 presents F-criterion values for all used substances. Subsequent intergroup comparisons (Bonferroni test) confirmed significant impact only in the group which administered claimed D-peptide.

TABLE 2

Impact of test products on tactile allodynia of rats. Tactile allodynia was assessed prior to injection of test products. Data are given as a mean value of paw withdrawal threshold (g) (M ± m).

| Group | Baseline | 60$^{th}$ day of products injection | 70$^{th}$ day of products injection | 80$^{th}$ day of products injection |
|---|---|---|---|---|
| Intact group | 28.82 ± 0.00 | 27.74 ± 0.80 | 26.94 ± 1.88 | 27.74 ± 0.80 |
| Control group | 28.82 ± 0.00 | 2.77 ± 0.71# | 3.10 ± 0.78# | 3.46 ± 0.61# |
| Byetta ® | 28.82 ± 0.00 | 5.72 ± 1.61 | 3.41 ± 0.55 | 6.59 ± 1.46 |

TABLE 2-continued

Impact of test products on tactile allodynia of rats. Tactile allodynia was assessed prior to injection of test products. Data are given as a mean value of paw withdrawal threshold (g) (M ± m).

| Group | Baseline | 60$^{th}$ day of products injection | 70$^{th}$ day of products injection | 80$^{th}$ day of products injection |
|---|---|---|---|---|
| Exenatide | 28.14 ± 0.69 | 5.33 ± 1.17 | 5.72 ± 1.18 | 8.24 ± 2.73 |
| D-peptide | 28.82 ± 0.00 | 16.15 ± 4.18* | 13.91 ± 3.59* | 15.05 ± 3.67* |
| Metformin | 28.82 ± 0.00 | 4.94 ± 0.90 | 4.98 ± 0.87 | 4.28 ± 0.45 |

Note-
differences are statistically significant in comparison with the intact group, t-test for independent variables with p < 0.05,
*differences are statistically significant in comparison with the control group, Bonferroni test with p < 0.05.

TABLE 3

Results of statistical data processing by expression of tactile allodynia on the background of injection of test products

| Indicator | F-criterion value | P-value |
|---|---|---|
| Control group | $F_{1;14}$ = 669.8 | <0.0001 |
| Byetta | $F_{1;14}$ = 5.78 | 0.03 |
| Exenatide | $F_{1;14}$ = 4.66 | 0.04 |
| D-peptide | $F_{1;14}$ = 22.52 | 0.0003 |
| Metformin | $F_{1;14}$ = 2.87 | 0.01 |

Thus, study of effects of test products showed the following: Byetta®, exenatide and Metformin decreased allodynia manifestation intensity slightly in individual comparison of indicators, however further intergroup comparison did not confirm statistically significant impact. Injection of claimed D-peptide starting from the 60$^{th}$ day of injection decreased tactile allodynia manifestations significantly on rats suffering from diabetic neuropathy (tables 2-3). This observation allows concluding that in case of long-term treatment (starting from the 60$^{th}$ day of injection) there is a certain therapeutic effect in relation to one of the most widespread complications DM 2, peripheral diabetic neuropathy which is probably conditioned by neuroprotective action of claimed D-peptide.

EXAMPLE 9

Assessment of Tactile Allodynia on Rats Suffering from Alcohol Neuropathy

Assessment of tactile allodynia was performed in the same way as in the example 7. Symptoms of alcohol neuropathy (tactile allodynia) were observed starting from the 8$^{th}$ week (56-60 days) of consumption of 30% alcohol by rats according to the method of forced drinking [40] ($F_{1;12}$=26.25; p=0.0003; FIG. 2) which indicates the established model of alcohol neuropathy with apparent pain syndrome.

Statistical processing by two-way analysis of variance with repeated measurements which allowed determining significance of the factor "injection of medicinal products" on development degree of tactile allodynia was carried out for further assessment of obtained results ($F_{1;10}$=8.79; p<0.014). Further intergroup comparison (post hoc) showed decrease in tactile allodynia intensity in the group which was treated with claimed D-peptide on the 100$^{th}$ day of injection, as compared to the control group in the corresponding measurement point (p<0.05; Bonferroni test; FIG. 2).

Summarizing all of the aforesaid, it may be concluded that claimed D-peptide has neuroprotective properties in relation to neurodegenerative processes developed during alcohol and diabetic peripheral neuropathy.

Pathomorphological Study

All experimental animals were subject to pathomorphological study in the end of the study.

Pathomorphological study comprised of necropsy, macroscopic examination, histologic examination of the following internal organs: central portion of sciatic nerve, retina artery, part of mesentery artery, part of gastrocnemius muscle, pancreatic gland. Necropsy was carried out under direct supervision of a pathologist. Samples of specified tissues were cut out and put into 10% solution of neutral formalin, while an eye bulb was fixed with a Davidson lock for 24 hours, then the material underwent standard treatment for production of histologic and histochemical specimens with thickness of serial paraffin sections of 5-7 µm. Tissue and organ sections for microscopic examination were stained with haematoxylin and eosin. Nerve tissue samples were stained with haematoxylin and eosin, toluidine blue by the Nissl's method and picro-fuchsin by the van Gieson's method. In order to reveal myelin fibers and myelin decay products, cross and longitudinal sections of nerves obtained on the freezing microtome were stained with Sudan black by the Lieson's method [41, 42, 43]. Nuclei were counterstained with hemalum. Samples of gastrocnemius muscle were stained with haematoxylin, eosin and picro-fuchsin by the van Gieson's method.

Morphological examination of histologic specimens was carried out using the light-optical microscope Carl Zeiss (Germany) with magnification of 100, 200 and 400. Microphotography was conducted using the digital camera Axio Scope A1 (Germany). Morphometry was carried out semi-automatically and manually using the software AxioVision Rel. 4.8. and image editor PhotoM 1.21.

In order to assess action of test substances, there was performed a comparative histologic evaluation of their impact on:
1. pancreatic gland insular apparatus where measurement of islets area was performed;
2. artery of muscular type and microcirculatory bloodstream (arterioles and capillaries) of retina, mesentery artery where morphometric measurement of capillary diameter and artery intima thickness was performed;
3. sciatic nerve condition;
4. somatic musculature condition.

EXAMPLE 10

Condition Assessment of Mesenteric Artery Intima of Rats

FIG. 3 presents data about impact of test substances on condition of mesenteric artery intima of rats. It was shown in paired comparison of the intact and control groups that significant increase in vessel intima thickness occurs in the control group (p<0.0001, t-test). This thickness increase and vessel intima swelling attests to development of endotheliopathy processes. Further one-way analysis of variance (ANOVA) showed that long-term injection of test substances prevents increase in vessel intima thickness of mesenteric artery of rats ($F_{4,25}$=12.87; p=0.0001). Intergroup comparison showed significant decrease of vessel intima thickness in all groups as compared to the control group (p<0.05, Bonferroni test). Maximum effect was observed in the group which administered claimed D-peptide (p<0.0001, Bonferroni test).

EXAMPLE 11

Condition Assessment of Sciatic Nerve Tissue

It may be concluded on the basis of established pathomorphological changes in nerve tissue that modeling of STZ-induced type 2 diabetes mellitus was accompanied by apparent condition of diabetic neuropathy which was characterized by decrease in thickness and diameter of nerve stems, deformation and swelling of myelin sheaths, affected nerve fibers, interstitial tissue edema, abnormal accumulation of lipids in epineurium and perineurium, as well as growth of endoneural connective tissue.

Individual fibers were in the condition of hydropic degeneration. Aggregates of small sudanophilic granules which indicated continuous myelin decay were observed in the foci of demyelination.

Injection of Metformin did not have a therapeutic effect on nerve tissue. Severe lesions of nerve stems and fibers, perineurium and epineurium manifested in apparent polymorphonuclear infiltration with focal degeneration of myelin sheaths, as well as swelling and deformation of fibers, occurrence of myelin decay products as sudanophilic granules adjoining to the basal membrane of unaffected myelin fibers were observed in tissue samples of this group.

When Byetta® and exenatide were injected, only an insignificant accumulation of lipids in perineurium and epineurium was observed. It is obvious that degenerative phenomena in this group were substantially lower or did not occur at all. On the contrary, injection of claimed D-peptide had a positive therapeutic effect, whereas apparent morphological differences in the structure of sciatic nerves from the group of intact animals were not revealed.

It was determined during pathomorphological analysis of nerve tissue indicators that the nerve stem thickness had significantly decreased in the control group as compared to intact animals (p<0.0001; t-test) which may indicate degenerative changes in the tissue and is proved by pathomorphological condition of pathology development (table 4).

TABLE 4

Morphometric indicators of nerve tissue under action of test substances

| Groups | Indicators | |
|---|---|---|
| | Nerve stem thickness, μm | Endoneurium connective tissue area, μm² |
| Intact | 340.5 ± 8.7 | 2,596.3 ± 74.1 |
| Control | 203.3 ± 6.9# | 3,962.5 ± 314.6# |
| Byetta ® | 213.2 ± 37.4 | 2,111.7 ± 239.9* |
| Exenatide | 256.8 ± 11.2 | 2,284.4 ± 211.5* |
| D-peptide | 303.6 ± 20.3* | 1,956.1 ± 273.4** |
| Metformin | 382 ± 23.4 | 2,826.3 ± 298.9* |

Note:
difference from the intact group (p < 0.05);
*difference from the control group (p < 0.05);
**difference from the control group (p < 0.01).

As noted above, pathomorphological condition of nerve tissue samples in the group which administered Metformin indicates nerve stem edema and excess increase of its thickness which implies pathology enhancement, but not therapeutic effect. Statistical analysis without inclusion of the abovementioned group was carried out in this connection. One-way analysis of variance (ANOVA) revealed significant impact of injection of test substances on nerve stem thickness ($F_{3,34}$=4.83; p=0.007). Further intergroup comparison (post hoc) confirmed significant increase in nerve stem thickness in the group which administered claimed D-peptide (p<0.01; Bonferroni test) as compared to the control group.

It was established in the analysis of such a pathomorphometric indicator as endoneurium connective tissue area that significant growth of endoneural connective tissue occurred upon pathology modeling (p<0.0018; t-test), which may indicate dominance of degenerative manifestations over reparative ones [Karpova and Krishtop, 2013]. Performance of one-way analysis of variance (ANOVA) showed significant impact of injection of test substances on endoneural connective tissue area ($F_{4,25}$=8.58; p=0.0002). Further intergroup comparison (post hoc) confirmed significant decrease of endoneural connective tissue area in all groups (p<0.01; Bonferroni test). Maximum effect was registered in groups which administered claimed D-peptide (p=0.0002; Bonferroni test) (table 4) that may be treated as enhancement of reparative processes in nerve tissue.

EXAMPLE 12

Condition Assessment of Muscle Tissue (Gastrocnemius Muscle)

It may be concluded on the basis of established pathomorphological changes in striated muscle tissue of gastrocnemius muscles that experimental DM 2 progression was accompanied by apparent condition of muscular dystrophy which was characterized by thinning and deformation of muscle fibers, moderate growth of surrounding connective tissue, in some cases with substitution of atrophied fibers with collagenous connective tissue, as well as increase in quantity of muscle cell nuclei (myonuclei). Moderate inflammatory infiltration was found in connective tissue of endomysium and perimysium on animals with fiber atrophy.

Focal growth of connective tissue with substitution of affected muscle fibers and moderate lymphocytic infiltration was observed in the group which administered Byetta® and exenatide. Minimum focal inflammatory infiltration of fibers and interstitial tissue was observed in the group which administered Metformin on the background of increase in myonuclear ratio.

On the background of established pathology, injection of claimed D-peptide had apparent therapeutic action on muscle tissue. Pathological changes were found in these groups in single cases and were minor as compared to the control group.

When analyzing cross section area of muscle fibers, it was established that progression of experimental DM of type 2 was accompanied by significant decrease in cross section area of muscle tissue fibers (p<0.0001; t-test) with concurrent decrease in quantity of myonuclei in fibers (about 70%) which may be treated as muscular dystrophy signs. Performance of one-way analysis of variance (ANOVA) showed significant impact of injection of test substances on cross section area of muscle fibers ($F_{4,22}$=13.67; p=0.0001). Further intergroup comparison (post hoc) confirmed that significant increase in cross section area of muscle fibers in all groups (p<0.01; Bonferroni test), except for the group which administered Byetta® (p=0.051; Bonferroni test). Maximum effect was registered in groups which administered exenatide (p<0.0001; Bonferroni test) and claimed D-peptide (p=0.0004; Bonferroni test) (table 5).

TABLE 5

Cross section area of muscle fibers of gastrocnemius muscle under the action of test substances, (M ± m)

| Groups | Cross section area of fibers, $\mu m^2$ |
| --- | --- |
| Intact | 1,450 ± 120 |
| Control | 551.1 ± 45[#] |
| Byetta ® | 968.3 ± 115 |
| Exenatide | 1,763 ± 142** |
| D-peptide | 1,472 ± 282* |
| Metformin | 1,286 ± 157* |

Note:
[#]difference from the intact group (p < 0.05);
*difference from the control group (p < 0.05);
**difference from the control group (p < 0.0001).

EXAMPLE 13

Pancreatic Gland Insular Apparatus

Table 6 presents summarized data about impact of test substances on the pancreatic gland insular apparatus of experimental animals. It was shown in paired comparison of the intact and control group that significant decrease of Langerhans islets occurs in the control group (p<0.0001, t-test). This decrease in insular apparatus area implies development of pathology which also correlates to increase of glucose level in peripheral blood. Paired comparison of the control group with experimental ones revealed statistically significant impact of injection of all test substances on area of pancreatic gland islets (table 7). This observation indicates that long-term injection of test substances causes increase of islets area and thus facilitates repair processes of the pancreatic gland insular apparatus.

TABLE 6

Morphometric indicators of condition of pancreatic gland insular apparatus after 80-day injection of test products.

| Groups | Area of pancreatic gland islets, $\mu m^2$ |
| --- | --- |
| Intact | 0.066 ± 0.008 |
| Control | 0.012 ± 0.002[#] |
| Byetta ® | 0.030 ± 0.006* |
| Exenatide | 0.030 ± 0.008* |

TABLE 6-continued

Morphometric indicators of condition of pancreatic gland insular apparatus after 80-day injection of test products.

| Groups | Area of pancreatic gland islets, $\mu m^2$ |
| --- | --- |
| D-peptide | 0.025 ± 0.004* |
| Metformin | 0.034 ± 0.004* |

Note:
[#]difference from the intact group (p < 0.05);
*difference from the control group (p < 0.05, t-test);

TABLE 7

Results of statistical processing of data on area of pancreatic gland islets after multiple injections of test products (Student's test)

| Indicator | P-value |
| --- | --- |
| Control group | p < 0.0001[#] |
| Byetta | p = 0.019* |
| Exenatide | p = 0.04 |
| D-peptide | p = 0.011* |
| Metformin | p = 0.001* |

Note:
[#]in comparison with the intact group of rats (p < 0.001)
*in comparison with the control group of rats (p < 0.05)

Thus, it was revealed in pathomorphological analysis of organs and tissues that modeling of Streptozotocin-induced type 2 diabetes mellitus was accompanied by endotheliopathy, decrease in area of the pancreatic gland insular apparatus as well as the apparent condition of development of diabetic peripheral neuropathy and dystrophic changes in striated thigh muscles.

Maximum and apparent therapeutic effect was observed after 80-day injection of claimed D-peptide. Injection of this compound had a positive curative action in respect of complications of type 2 diabetes mellitus, such as diabetic neuropathy, muscular dystrophy, endotheliopathy, and had favorable impact on reparative processes in the pancreatic gland insular apparatus. Analysis of histologic samples is correlated to clinical data. In particular, apparent curative effect was observed in manifestation of allodynia signs and decrease in glycosylated hemoglobin content in red blood cells of experimental animals. Apparent antihyperglycemic action of this compound which was comparable with that of Metformin was also noticed.

In view of the aforesaid, it can be concluded that claimed D-peptide is a highly-effective agent for therapy and prevention of type 2 diabetes mellitus complications, especially diabetic neuropathy, and has neuroprotective action as to alcohol neuropathy.

LIST OF REFERENCES

1. Stern, M. P., Williams, K., Gonzalez-Villalpando, C., Hunt, K. J., Haffner, S. M., 2004. Does the metabolic syndrome improve identification of individuals at risk of type 2 diabetes and/or cardiovascular disease? Diabetes Care 27, 2676-2681.

2. Fu, W., Patel, A., Jhamandas, J. H., 2013. Amylin receptor: a common pathophysiological target in Alzheimer's disease and diabetes mellitus. Front Aging Neurosci. 5, 42.

3. Danaei, G., Finucane, M. M., Lu, Y., Singh, G. M., Cowan, M. J., Paciorek C. J., Lin, J. K., Farzadfar, F., Khang, Y. H., Stevens, G. A., Rao, M., Ali, M. K., Riley, L. M., Robinson, C. A., Ezzati, M., 2011. National, regional, and global trends in fasting plasma glucose and diabetes prevalence since 1980: systematic analysis of health examination surveys and epidemiological studies with 370 country-years and 2.7 million participants. Lancet 378, 31-40.

4. Global health risks. Mortality and burden of disease attributable to selected major risks. Geneva, World Health Organization, 2009.

5. Mathers, C. D., Loncar, D., 2006. Projections of global mortality and burden of disease from 2002 to 2030. PLoS. Med. 3, e442.

6. Nedosugova, L. V. Pathogenesis, clinical aspects, approaches to treatment of diabetic polyneuropathy//Meditsinsky Sovet, 12. 2013. P. 43-49.

7. Eng., J. et al., Isolation and Characterization of Exendin-4, an Exendin-3 Analogue, from *Heloderma suspectum* Venom. J. Biol. Chem., Vol. 267, Issue 11, 7402-7405, April, 1992.

8. U.S. Pat. No. 5,424,286 Exendin-3 and exendin-4 polypeptides, and pharmaceutical compositions comprising same 9. US 2005043238 Exendin formulations for weight reduction 10. U.S. Pat. No. 6,858,576 Method for regulating gastrointestinal motility 11. U.S. Pat. No. 9,800,449 Use of exendins and agonists thereof for the reduction of food intake 12. US 2005037958 Inotropic and diuretic effects of GLP-1 and GLP-1 agonists 13. U.S. Pat. No. 6,703,359 Inotropic and diuretic effects of exendin 14. JP 2002509078 Inotropic and diuretic effects of exendin and GLP-1

15. US 2004266678 Methods and compositions for treating polycystic ovary syndrome 16. MX 2008015640 Compounds for treatment of metabolic disorders 17. US 2009291100 Therapeutic agent for polycystic ovary syndrome (PCOS)

18. JP 2006520747 Methods and compositions for treating polycystic ovary syndrome 19. US 2004209803 Compositions for the treatment and prevention of nephropathy 20. AU 2003297356 Prevention and treatment of cardiac arrhythmias 21. AU 2003262628 Bone marrow cell differentiation 22. US 2004092443 Long-acting exendins and exendin agonists 23. US 2004023871 Use of exendins and agonists thereof for the treatment of gestational diabetes mellitus.

24. JP 2003519667 Use of exendins and agonists thereof for modulation of triglyceride levels and treatment of dyslipidemia 25. US 2003036504 Use of exendins and agonists thereof for modulation of triglyceride levels and treatment of dyslipidemia 26. U.S. Pat. No. 9,410,225 Method for regulating gastrointestinal motility 27. RU 2247575 Method for inhibiting glucagon 28. US 2007041951 Differentiation of non-insulin producing cells into insulin producing cells by GLP-1 or exendin-4 and uses thereof 29. PT 1019077 Novel exendin agonist compounds 30. LU 91342 Use of exendins and agonists thereof for the reduction of food intake 31. US 2002137666 Use of exendins and agonists thereof for the reduction of food intake 32. US 2006194719 Stabilized exendin-4 compounds 33. US 2003087821 Exendins, exendin agonists, and methods for their use 34. EP 1419783 Use of a composition comprising an exendin or a compound derived therefrom and a pharmaceutical carrier 35. Szkudelski T. Streptozotocin-nicotinamide-induced diabetes in the rat//Characteristics of the experimental model. Exp Biol Med (Maywood). 2012; 237(5):481-90.

36. Altman D. G. Bland J. M. How to randomize//BMJ. 1999. Vol. 11. p. 319 (7211)

37. Guidance on non-clinical studies of drug products// Federal State Budgetary Institution "Scientific Center for Evaluation of Medical Products". Under the editorship of A. N. Mironov. Vol. 1. 2012. 695 p.

38. Chaplan, S. R., et al. "Quantitative assessment of tactile allodynia in the rat paw".//J. Neurosci. Methods 53.1 (1994): 55-63.

39. Dixon W. J. Efficient analysis of experimental observations//Ann. Rev. Pharmacol. Toxicol.—1980.—Vol. 20.—P. 441-462.

40. Weiss, F., and Koob, G. F. The neuropharmacology of ethanol self-administration.//In: Meyer, R. E.; Koob, G. F.; Lewis, M. J.; and Paul, S. M., eds. Neuropharmacology of Ethanol: New Approaches./Boston: Birkhauser, 1991. pp. 125-162.

41. Kozyrev, K. M., Marzaganova, Z. A., Dzitstsoeva, P. A. Comparative clinicopathologic characteristics of Pick's disease and Alzheimer's disease//Bulletin of New Medical Technologies. 2013. No. 1, 7 p.

42. Makhmutov, O. K. Reactive changes in nerves at early stages of conduction anesthesia//Veterinarny Doktor, 2007. P. 23-25.

43. Chumasov, E. I. Methodological developments on diagnosis of human and animal demyelinating diseases. 1993. P. 1-16

The invention claimed is:

1. A compound having the formula: H-His-Gly-Glu-Gly-Thr-Phe-Thr-Ser-Asp-Leu-Ser-Lys-Gln-Gly-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-D-Arg-D-Arg-D-Arg-D-Arg-D-Arg-D- Arg-D-Arg-D-Arg-Gly-OH.

2. A method of at least one of treating or preventing type 2 diabetes, diabetic neuropathy, and complications of type 2 diabetes, the method comprising administering a compound according to claim 1 to a patient in need thereof.

* * * * *